(12) United States Patent
Katsuki

(10) Patent No.: US 11,901,045 B2
(45) Date of Patent: Feb. 13, 2024

(54) MACHINE LEARNING FRAMEWORK FOR FINDING MATERIALS WITH DESIRED PROPERTIES

(71) Applicant: INTERNATIONAL BUSINESS MACHINES CORPORATION, Armonk, NY (US)

(72) Inventor: Takayuki Katsuki, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1167 days.

(21) Appl. No.: 16/247,954

(22) Filed: Jan. 15, 2019

(65) Prior Publication Data

US 2020/0227143 A1 Jul. 16, 2020

(51) Int. Cl.
*G16C 20/30* (2019.01)
*G16C 20/70* (2019.01)
*G06N 5/04* (2023.01)
*G06N 20/10* (2019.01)

(52) U.S. Cl.
CPC ............. *G16C 20/30* (2019.02); *G06N 5/04* (2013.01); *G06N 20/10* (2019.01); *G16C 20/70* (2019.02)

(58) Field of Classification Search
None
See application file for complete search history.

(56) References Cited

U.S. PATENT DOCUMENTS

| 8,452,716 | B2 | 5/2013 | Howley et al. | |
|---|---|---|---|---|
| 2008/0168014 | A1* | 7/2008 | Bhagat | G06N 3/02 706/20 |
| 2013/0173503 | A1 | 7/2013 | Segall et al. | |
| 2017/0058004 | A1* | 3/2017 | Stratis-Cullum | C12N 15/74 |

(Continued)

FOREIGN PATENT DOCUMENTS

| JP | 2007018444 A | 1/2007 |
|---|---|---|
| JP | 2007106708 A | 4/2007 |

(Continued)

OTHER PUBLICATIONS

JP-2021039534-A_Translated (Year: 2021).*

(Continued)

*Primary Examiner* — Manish S Shah
*Assistant Examiner* — Michael J Singletary
(74) *Attorney, Agent, or Firm* — Tutunjian & Bitetto, P.C.; Robert Richard Aragona

(57) ABSTRACT

A computer-implemented method is presented for discovering new material candidates from a chemical database. The method includes extracting a feature vector from a chemical formula, learning a prediction model for predicting property values from the feature vector with a sparse kernel model employing the chemical database, selecting an existing material from a list of existing materials sorted in descending order based on the predicted property values by the prediction model learned in the learning step, selecting a basis material from a list of basis materials sorted in descending order of absolute reaction magnitudes to the selected existing material, and generating the new material candidates as variants of the selected existing material with consideration of the selected basis material.

20 Claims, 7 Drawing Sheets

(56) References Cited

U.S. PATENT DOCUMENTS

2017/0124482 A1\* 5/2017 Yoo .................. G06N 7/005
2018/0032663 A1\* 2/2018 Yoo .................. G06N 20/00

FOREIGN PATENT DOCUMENTS

| JP | 2007511470 A | | 5/2007 |
|----|--------------|---|--------|
| JP | 2016052305 A | | 4/2016 |
| JP | 2017091526 A | | 5/2017 |
| JP | 2021039534 A | \* | 3/2021 |

OTHER PUBLICATIONS

Liu et al., "Deep Learning for Chemical Compound Stability Prediction", Proceedings of ACM SIGKDD Workshop on Large-Scale Deep Learning for Data Mining. Aug. 13-17, 2016. pp. 1-7.
Liu et al., "Materials discovery and design using machine learning", Journal of Materiomics. vol. 3. Sep. 1, 2017. pp. 159-177.
Ward et al., "A General-Purpose Machine Learning Framework for Predicting Properties of Inorganic Materials", npj Computational Materials. vol. 2. Aug. 26, 2016. pp. 1-23.
International Search Report and Written Opinion with cited art in corresponding UK Application PCT/IB2019/060838 dated Apr. 17, 2020.
Notice of Reasons for Refusal for JP2021531184 dated Jun. 28, 2023 (3 pages).

\* cited by examiner $$\arg\max_{\mathbf{z}} \mathbf{w}^\top \phi(\mathbf{x}(\mathbf{z}))$$

z: chemical formula
x(z): feature vector (arbitrary)
φ(x(z)): basis function (based on distance, e.g., radial basis function)

510

$$\frac{\partial \mathbf{w}^\top \phi(\mathbf{x}(\mathbf{z}))}{\partial \mathbf{z}}$$
$$\propto \sum_j w_j \exp\left(-\frac{1}{2\sigma^2}\|\mathbf{x}(\mathbf{z}) - \mathbf{x}_j\|^2\right)\left(-\frac{\partial}{\partial \mathbf{z}}\|\mathbf{x}(\mathbf{z}) - \mathbf{x}_j\|\right)$$

MACHINE LEARNING FRAMEWORK FOR FINDING MATERIALS WITH DESIRED PROPERTIES

BACKGROUND

Technical Field

The present invention relates generally to discovering new materials, and more specifically, to a machine learning framework for finding new materials with desired properties.

Description of the Related Art

The practice of data mining, in light of the availability of large-scale data, has been causing a paradigm change in scientific discovery, from empirical science to theoretical, computational science, and now to data science. Specifically, there are spurring interests in applying advanced machine learning techniques to assist materials discovery which envisions computationally assisted discovery, development, manufacturing, and deployment of advanced materials at a much accelerated speed and reduced cost. Real-world applications encourage the development of methods that help objectively create new materials with desired properties for specific applications, by linking what a person sees (e.g., structure of a crystal, composition of a compound) to what a person wants (e.g., a certain strength demand of an alloy).

SUMMARY

In accordance with an embodiment, a method is provided for discovering new material candidates from a chemical database. The method includes extracting a feature vector from a chemical formula, learning a prediction model for predicting property values from the feature vector with a sparse kernel model employing the chemical database, selecting an existing material from a list of existing materials sorted in descending order based on the predicted property values by the prediction model learned in the learning step, selecting a basis material from a list of basis materials sorted in descending order of absolute reaction magnitudes to the selected existing material, and generating the new material candidates as variants of the selected existing material with consideration of the selected basis material.

In accordance with another embodiment, a system is provided for discovering new material candidates from a chemical database. The system includes a memory and one or more processors in communication with the memory configured to employ a feature vector extracted from a chemical formula, learn a prediction model for predicting property values from the feature vector with a sparse kernel model employing the chemical database, select an existing material from a list of existing materials sorted in descending order based on the predicted property values by the prediction model learned in the learning step, select a basis material from a list of basis materials sorted in descending order of absolute reaction magnitudes to the selected existing material, and generate the new material candidates as variants of the selected existing material with consideration of the selected basis material.

In accordance with yet another embodiment, a non-transitory computer-readable storage medium comprising a computer-readable program for discovering new material candidates from a chemical database is presented. The non-transitory computer-readable storage medium performs the steps of extracting a feature vector from a chemical formula, learning a prediction model for predicting property values from the feature vector with a sparse kernel model employing the chemical database, selecting an existing material from a list of existing materials sorted in descending order based on the predicted property values by the prediction model learned in the learning step, selecting a basis material from a list of basis materials sorted in descending order of absolute reaction magnitudes to the selected existing material, and generating the new material candidates as variants of the selected existing material with consideration of the selected basis material.

It should be noted that the exemplary embodiments are described with reference to different subject-matters. In particular, some embodiments are described with reference to method type claims whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be described within this document.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The invention will provide details in the following description of preferred embodiments with reference to the following figures wherein:

FIG. 5 is a block/flow diagram of an exemplary equation for implementing the deterministic generation method for discovering material candidates, in accordance with an embodiment of the present invention;

Throughout the drawings, same or similar reference numerals represent the same or similar elements.

DETAILED DESCRIPTION

Figure 1:
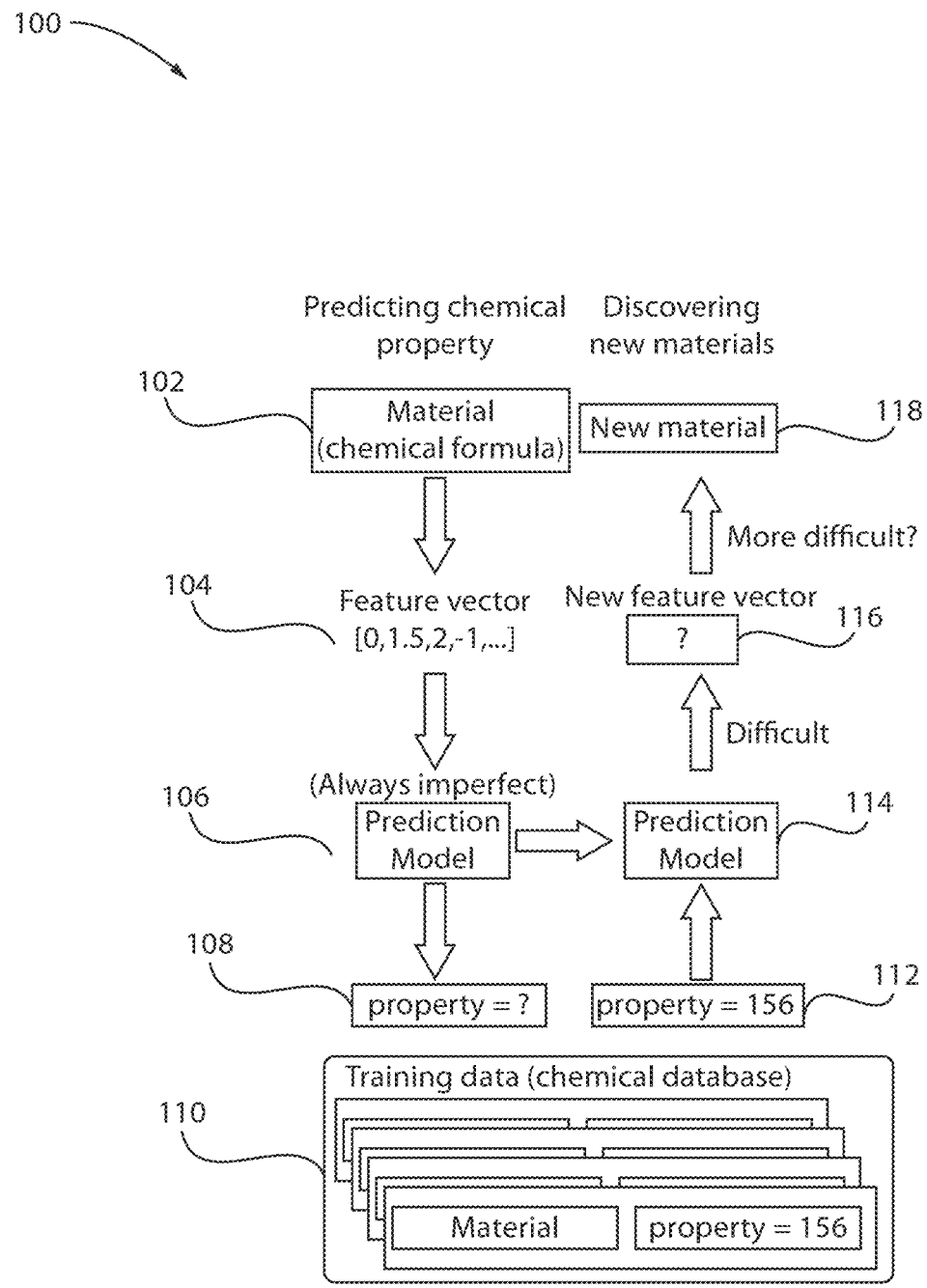
FIG. 1 is an exemplary deterministic generation method for discovering material candidates.

Embodiments in accordance with the present invention provide methods and devices for employing a deterministic method without randomness for generating new material candidates by using a sparse kernel model, where the method generates the candidates as variants between the existing materials having higher target property values and the basis materials having large reaction magnitudes to these existing materials in the sparse kernel model.

The issue with materials discovery relates to deciding on certain composition, formulation, and processing steps of materials with a desired target property. Neural networks as a tool have been used in materials science applications such as spectroscopy classification and structural identification, characterizing constitutive relationships for alloys, the evaluation of descriptors, etc. However, neural networks, and deep learning, have not been extensively used in materials discovery applications. The exemplary embodiments of the present invention employ deep learning techniques to discover new materials with desired properties.

Machine learning techniques are more effective as compared with statistical techniques to detect and analyze time-series data. This is because machine learning has two important features, that is, feature engineering and prediction. The feature engineering aspect is used to address the trend and seasonality issues of time series data. The issues of fitting the model to time series data can also be resolved by it.

Deep learning is used to combine the feature extraction of time series with a non-linear autoregressive model for higher level prediction. Deep learning is used to extract useful information from the features automatically without using any human effort or complex statistical techniques.

There are two most effective techniques of machine learning, that is, supervised and unsupervised learning. Supervised learning is performed for training data points so that they can be classified into different categories of data points. But, for supervised learning, data points need to be labeled. However, another approach is unsupervised learning where the data points are not labeled. One can apply unsupervised learning to train a system so that prediction of next data points in the series could be made. To implement this, a confidence interval or prediction error is made. Therefore, to data points, a test can be implemented to check which data points are present within or outside the confidence interval. The most common supervised learning algorithms are supervised neural networks, support vector machine learning, k-nearest neighbors, Bayesian networks and decision trees. The most common unsupervised algorithms are self-organizing maps (SOM), K-means, C-means, expectation-maximization meta-algorithm (EM), adaptive resonance theory (ART), and one-class support vector machine.

It is to be understood that the present invention will be described in terms of a given illustrative architecture; however, other architectures, structures, substrate materials and process features and steps/blocks can be varied within the scope of the present invention. It should be noted that certain features cannot be shown in all figures for the sake of clarity. This is not intended to be interpreted as a limitation of any particular embodiment, or illustration, or scope of the claims.

FIG. 1 is an exemplary deterministic generation method for discovering material candidates.

Discovering new materials with desired properties (e.g., high glass transition temperature, low viscosity, etc.) is an important task for chemical industries. There are many similar problems and needs (inverse analysis) in various domains, such as generating recipes (for chemical reaction, cooking, fragrance, etc.), optimizing physical structures, advertisement, etc.

The issue is discovering or finding materials having a high property value from a chemical database, as shown in flowchart 100 of FIG. 1. The input 102 includes pairs of existing materials (e.g., a chemical formula) and corresponding properties of the chemical formula. The output 118 includes a chemical formula of a new material having the desired properties, where the desired property can be, e.g. a high value. However, the desired property can be generalized to other settings, such as exploring materials having a particular property value.

In conventional methods, the following steps can be performed in a batch manner or sequential manner. In a first step, construct a prediction model 106 for a chemical property from some feature vector 104 extracted from a chemical formula 102. In a second step, optimize (inverse analyze) the feature vector 104 based on the prediction model 106. In a third step, convert the vector into a chemical formula. In one instance, a property value 108 can be selected from a training database 110. The selected property value can be, e.g., property value 112. The property value 112 can be fed back into the prediction model 114, from which a new feature vector 116 needs to be converted into a new material 118. The conversion from the new feature vector 116 to the new material 118 can be very difficult.

As a result, these methods need less computational cost for the experiments or need sufficient training data for learning a good response or result. Moreover, extrapolation can be nonsensical and it can be difficult to convert the feature vector into a chemical formula. Therefore, certain assumptions can be made, that is, that conventional methods cannot directly solve the issue of predicting a chemical formula from a property (or property value), and that conventional methods cannot directly employ a 3D structure for the input of the prediction model for the property (or property value) because of the insufficiency of the training data stored in the training database 110.

Figure 2:
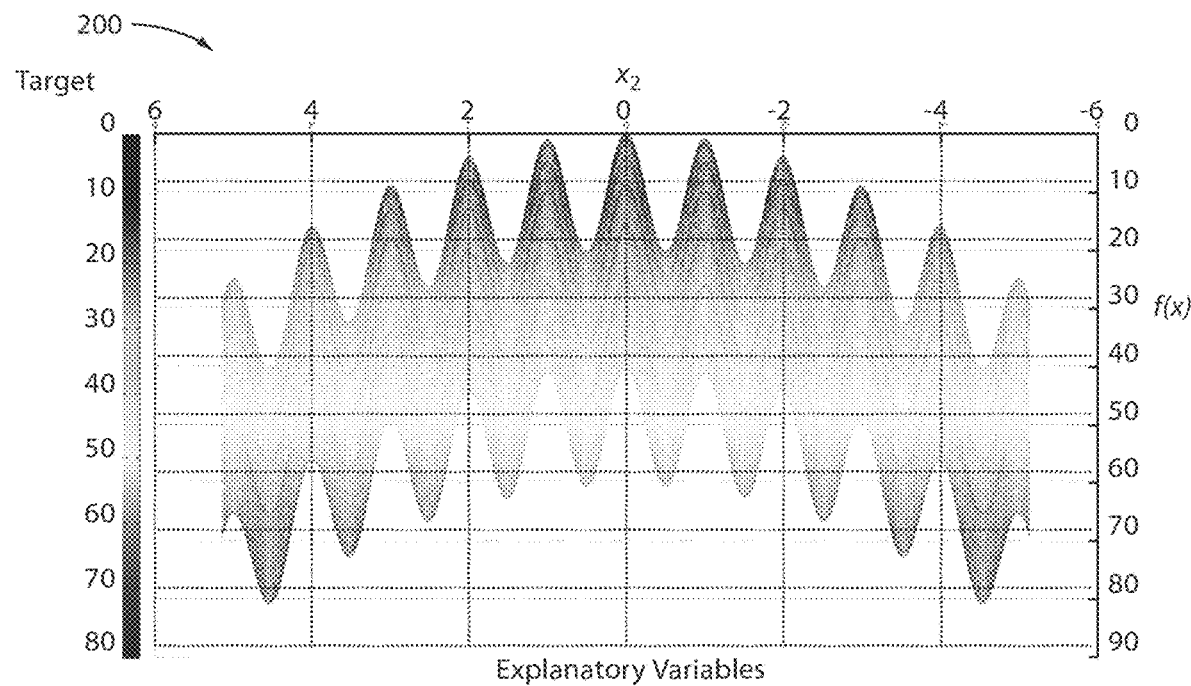
FIG. 2 is an exemplary graph illustrating sampling of the training data, in accordance with an embodiment of the present invention.
Figure 3:
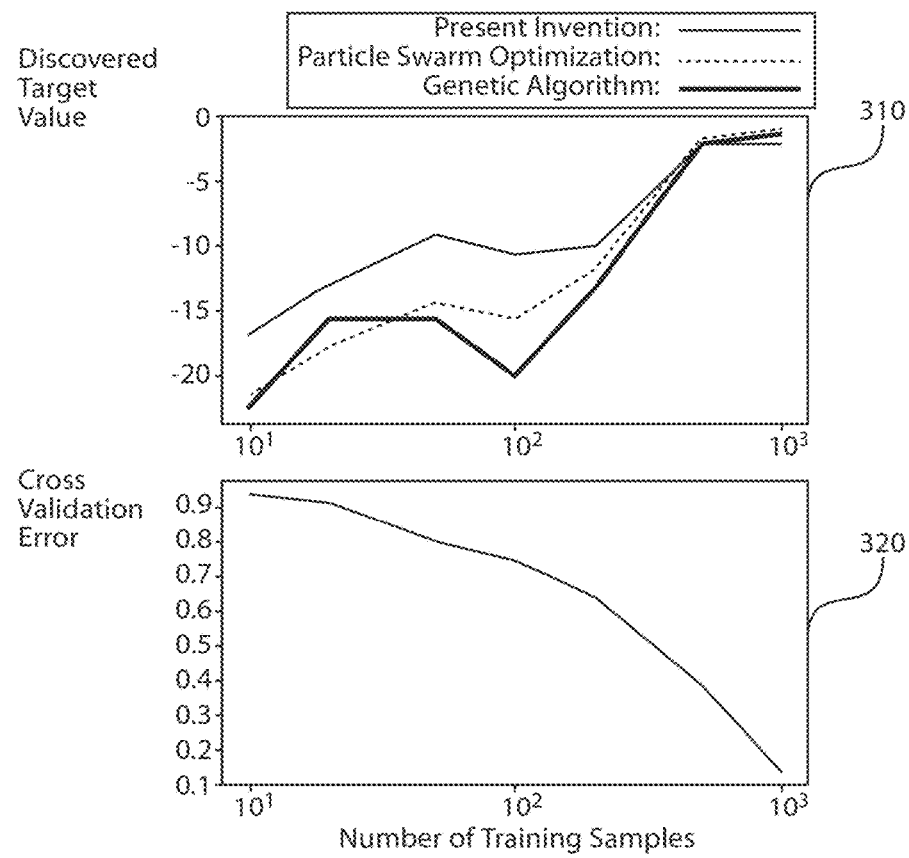
FIG. 3 is an exemplary graph comparing the present method with prior methods, in accordance with an embodiment of the present invention.

FIG. 2 is an exemplary graph illustrating sampling of the training data, in accordance with an embodiment of the present invention, whereas FIG. 3 is an exemplary graph comparing the present method with prior methods, in accordance with an embodiment of the present invention.

Instead of employing the graph 100 of FIG. 1, the exemplary embodiments employ a prediction model for property values from a feature vector of a material and directly explore a chemical-formula of new material candidates in the interpolation area of the prediction model (without the need to convert the feature vector into a new material, as in FIG. 1). Therefore, the exemplary embodiments of the present invention employ a sparse kernel model for the predicting model that predicts the properties or property values from the materials. By employing the sparse kernel model, the methods explore and discover materials between the training data having good properties and the most reacted basis materials in the prediction model.

The materials in the training data can come from two sources: empirical experiments and computational simulations. Experimental data refer to the trial-and-error iterations of experimental observations, examples being microscopic images taken directly from a materials sample. Such data are often very limited in the size and can include noise of nonstationary variance affecting the data quality. Simulation data, on the other hand, are more abundant, available, stable, and less prone to human operation errors.

Regarding the term "kernel model," a kernel model can be derived from a kernel function. A kernel function takes as its inputs vectors in the original space and returns the dot product of the vectors in the feature space. Kernel methods are a class of algorithms for pattern analysis. The general task of pattern analysis is to find and study general types of relations (for example clusters, rankings, principal components, correlations, classifications) in datasets. In its simplest form, the kernel trick means transforming data into another dimension that has a clear dividing margin between classes of data. For many algorithms that solve these tasks, the data in raw representation have to be explicitly transformed into feature vector representations via a user-specified feature map. In contrast, kernel methods need only a user-specified kernel, i.e., a similarity function over pairs of data points in raw representation. Thus, kernel functions provide a way to manipulate data as though it were projected into a higher dimensional space, by operating on it in its original space.

Regarding the term "basis material," a composite material or compound material is a material made from two or more constituent materials (or basis materials) with significantly different physical or chemical properties that, when combined, produce a material with characteristics different from the individual components. The individual components remain separate and distinct within the finished structure. The new material can be preferred for many reasons, e.g., stronger, lighter, or less expensive when compared to traditional materials. Therefore, the basis materials can be considered constituent materials of composite materials.

In a first step, the method employs a feature vector that is extracted from a chemical formula and learns the model for predicting the properties from the feature vector with a sparse kernel model using a chemical database.

The feature vector is arbitrary (e.g., substructure count, structural feature, etc.). The feature vector does not require the consideration of ease of converting the feature vector into a material.

Moreover, the dimension reduction method for the feature vector can be used, which does not affect the algorithm.

The exemplary methods can employ a support vector machine (SVM), a relevance vector machine (RVM), and other models for the sparse kernel model, but Bayesian models (such as RVM) are better suited because such exemplary methods can use the posterior and confidence of the prediction and can further use a Bayesian optimization procedure in candidate generation.

SVM is a supervised machine learning technique that can be used for classification tasks. In its basic form, SVM represents the instances of the data into space and SVM tries to separate the distinct classes by a maximum possible wide gap (hyper plane) that separates the classes. On the other hand, RVM uses probabilistic measures to define this separation space. In one instance, RVM uses Bayesian inference to obtain a solution. Thus, RVM uses significantly fewer basis functions.

Moreover, the exemplary methods employ the kernel based on distances between data points in a feature space, without the need to know the coordinates of the data points in the feature space.

In a second step, the existing material is selected in descending order based on the predicted property values by the prediction model learned in the first step. Stated differently, a material list is created and is sorted based on the property values predicted by the prediction model. The descending order can be materials exhibiting the closest desired property values listed at the top and materials exhibiting relevant desired property values listed at the bottom. The descending order can be assembled as absolute closest, somewhat close, least closest, etc.

In some models (such as RVM), since the prediction for the training data is needed in the learning step, there are no additional computations for this prediction, only sorting.

The exemplary method can employ existing materials having no property labels for this step with additional prediction computations. The lack of property labels lends the methods to unsupervised learning techniques.

In a third step, the basis material is selected (from materials in the training database) in descending order of their absolute reaction magnitudes to the selected material in the second step (distance between the selected material and the basis×coefficient for the basis). Stated differently, a material list is created and is sorted based on absolute reaction magnitudes to the selected existing material.

From sparse modeling, a limited number of basis materials are activated.

In a fourth step, the exemplary method generates the new material candidates as the variants of the selected existing material in the second step and the selected basis material in the third step as follows:

If the reaction in the third step is positive, the exemplary methods "swap" the substructure between them as one of or a combination of the following: add the substructures of one material, which is not included in the other material, to the other material, or subtract the substructures, which are not shared between the materials.

If the reaction in the third step is negative, the exemplary methods subtract the substructures, which share the materials.

Steps 2 to 4 are repeated until a predetermined number of candidate materials have been derived. The predetermined number can be determined by a user or can be predefined by the software.

Since the exemplary methods generate the candidates as the variants between the existing data, the exemplary methods can generate the candidates mostly as interpolation of the prediction model. Exploration becomes broader according to the number and variation of the training data.

The exemplary embodiments of the present invention capture the nature that chemical formulae can change the structure discretely but not continuously.

In the sparse kernel model, the model has no information other than basis having non-zero weights through sparse learning. In general, the basis having non-zero weights will not resemble each other in most cases, and the material and the basis highly reacted to the material resemble each other because of the definition of the kernel (distance) in most cases.

Thus, just swapping materials having good properties will not be more efficient than the exemplary method. Moreover, the exemplary method can be applied sequentially and does not need to assume differentiability of the prediction model.

Regarding FIGS. 2 and 3, the exemplary methods sampled the training data from the function as shown in graph 200, learned the prediction model, and explored the high value of the function based on the prediction model.

The exemplary methods were compared with conventional methods, e.g., with particle swarm optimization (pattern 2) and genetic algorithm (pattern 3).

The exemplary methods further show the discovered target value and mean error of ten-fold cross-validation for each experimental setting in different number of training data as shown in graphs 310 and 320 of FIG. 3.

The performance of the exemplary method (pattern 1) was better than those of the other methods (patterns 2 and 3) especially in the setting where a small or insufficient number of training data is available.

Thus, the exemplary method is efficient compared to the other methods because the exemplary method has no randomness in its algorithm. In experiments on real chemical data, it has been determined that the sparse kernel model (e.g., RVM) has better prediction performance than other methods (e.g., linear model, random forest, etc.). The exemplary method discovered the new candidates with better performance than those found in the training database. Moreover, in one instance, it was determined that ⅓ of the discovered candidates overlapped with new materials.

Figure 4:
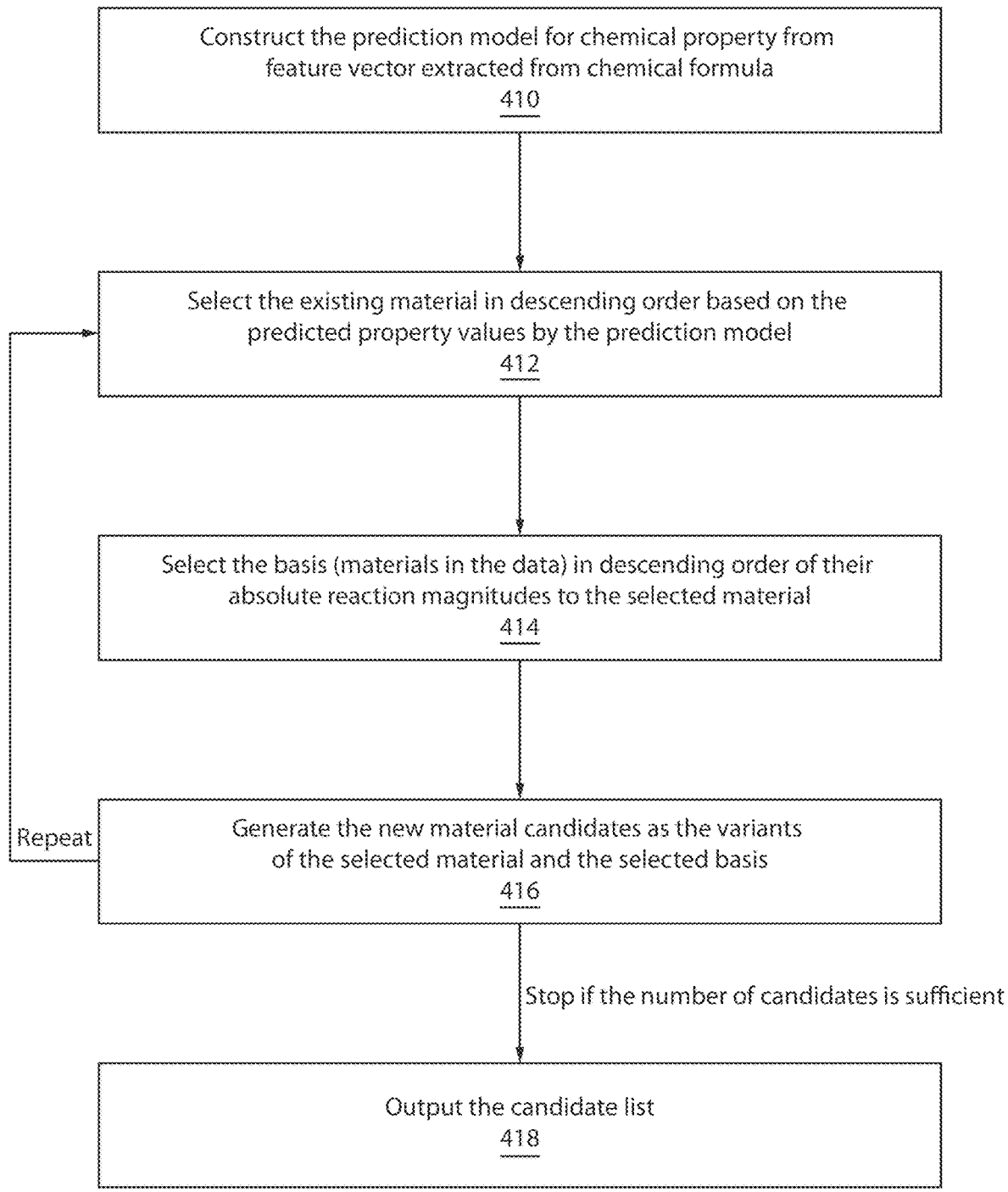
FIG. 4 is a block/flow diagram of an exemplary deterministic generation method for discovering material candidates by employing a sparse kernel model, in accordance with an embodiment of the present invention.

FIG. 4 is a block/flow diagram of an exemplary deterministic generation method for discovering material candidates by employing a sparse kernel model, in accordance with an embodiment of the present invention.

At block 410, the prediction model for the chemical property is constructed from a feature vector extracted from a chemical formula.

At block 412, the existing material is selected in descending order based on the predicted property values derived from the prediction model.

At block 414, the basis material (selected from materials in the training data) is selected in descending order of absolute reaction magnitudes to the selected existing material.

At block 416, the new material candidates are generated as the variants of the selected existing material and the selected basis material. If the number of candidates is sufficient, the process ends and proceeds to block 418.

At block 418, the candidate list is output, e.g., to a user interface of a computing device to be evaluated and analyzed.

FIG. 5 is a block/flow diagram of an exemplary equation for implementing the deterministic generation method for discovering material candidates, in accordance with an embodiment of the present invention.

The exemplary method can be approximately seen as the one-step ascent from the existing material in the following optimization problem 510:

$$\text{argmax}_z w^T \phi(x(z))$$

Where z is the chemical formula, x(z) is the feature vector (arbitrary), and $\Phi(x(z))$ is the basis function (based on distance, e.g., radial basis function).

The gradient 520 can be given as:

$$\frac{\partial w^T \phi(x(z))}{\partial z} \propto \sum_j w_j \exp\left(-\frac{1}{2\sigma^2}\|x(z) - x_j\|^2\right)\left(-\frac{\partial}{\partial z}\|x(z) - x_j\|\right)$$

In conclusion, the properties of materials, such as, e.g., hardness, melting point, ionic conductivity, glass transition temperature, molecular atomization energy, and lattice constant, can be described at either the macroscopic or microscopic level. There are two common methods of studying materials properties: computational simulation and experimental measurement. These methods involve complicated operations and experimental setup. Therefore, it is quite difficult to build computational simulations that fully capture the complicated logical relationships between the properties of a material and their related factors, and some of these relationships may even be unknown. Moreover, the experiments that are performed to measure the properties of compounds generally occur in the later stages of materials selection. Consequently, if the results are not satisfactory, the enormous amounts of time and experimental resources invested up to that point can prove to be fruitless. In addition, in many cases, it is difficult or nearly impossible to study the properties of materials even through massive computational or experimental efforts. Therefore, there is a need to develop intelligent and high-performance prediction models that can correctly predict the properties of materials at a low computational cost. Machine learning concerns the construction and study of algorithms that can learn patterns from data. The basic idea of using machine learning methods for material property prediction is to analyze and map the relationships (nonlinear in most cases) between the properties of a material and their related factors by extracting knowledge from existing empirical data. However, the empirical data can be insufficient. As a result, the exemplary embodiments of the present invention employ a machine learning framework for implementing a deterministic method without randomness for generating new material candidates by using a sparse kernel model, where the methods generate the candidates as variants between the existing materials having higher target property values and the basis materials having large reaction magnitudes to the existing materials in the sparse kernel model.

Figure 6:
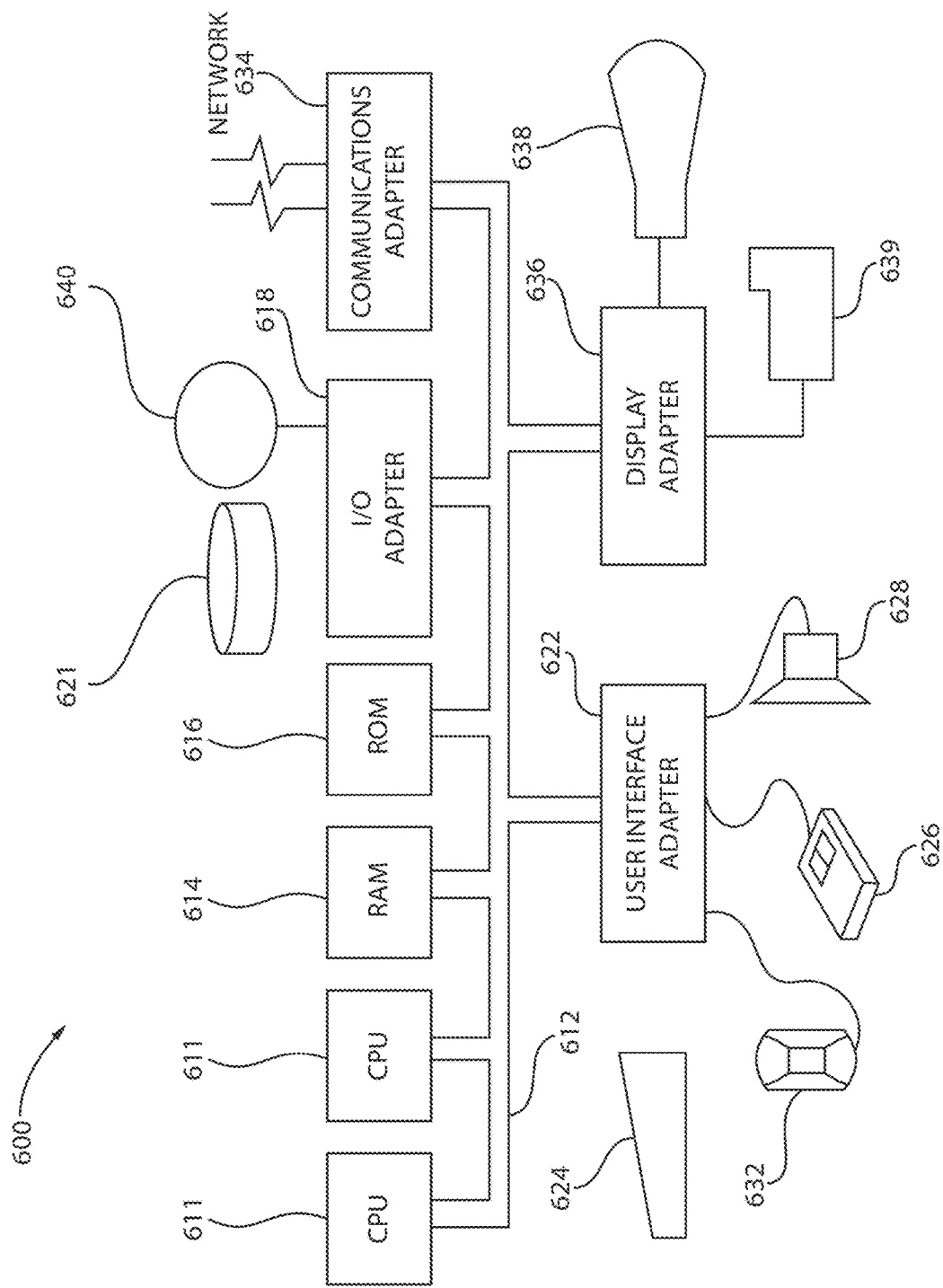
FIG. 6 is an exemplary processing system, in accordance with embodiments of the present invention.

FIG. 6 is an exemplary processing system, in accordance with embodiments of the present invention.

Referring now to FIG. 6, this figure shows a hardware configuration of computing system 600 according to an embodiment of the present invention. As seen, this hardware configuration has at least one processor or central processing unit (CPU) 611. The CPUs 611 are interconnected via a system bus 612 to a random access memory (RAM) 614, read-only memory (ROM) 616, input/output (I/O) adapter 618 (for connecting peripheral devices such as disk units 621 and tape drives 640 to the bus 612), user interface adapter 622 (for connecting a keyboard 624, mouse 626, speaker 628, microphone 632, and/or other user interface device to the bus 612), a communications adapter 634 for connecting the system 600 to a data processing network, the Internet, an Intranet, a local area network (LAN), etc., and a display adapter 636 for connecting the bus 612 to a display device 638 and/or printer 639 (e.g., a digital printer or the like).

Figure 7:
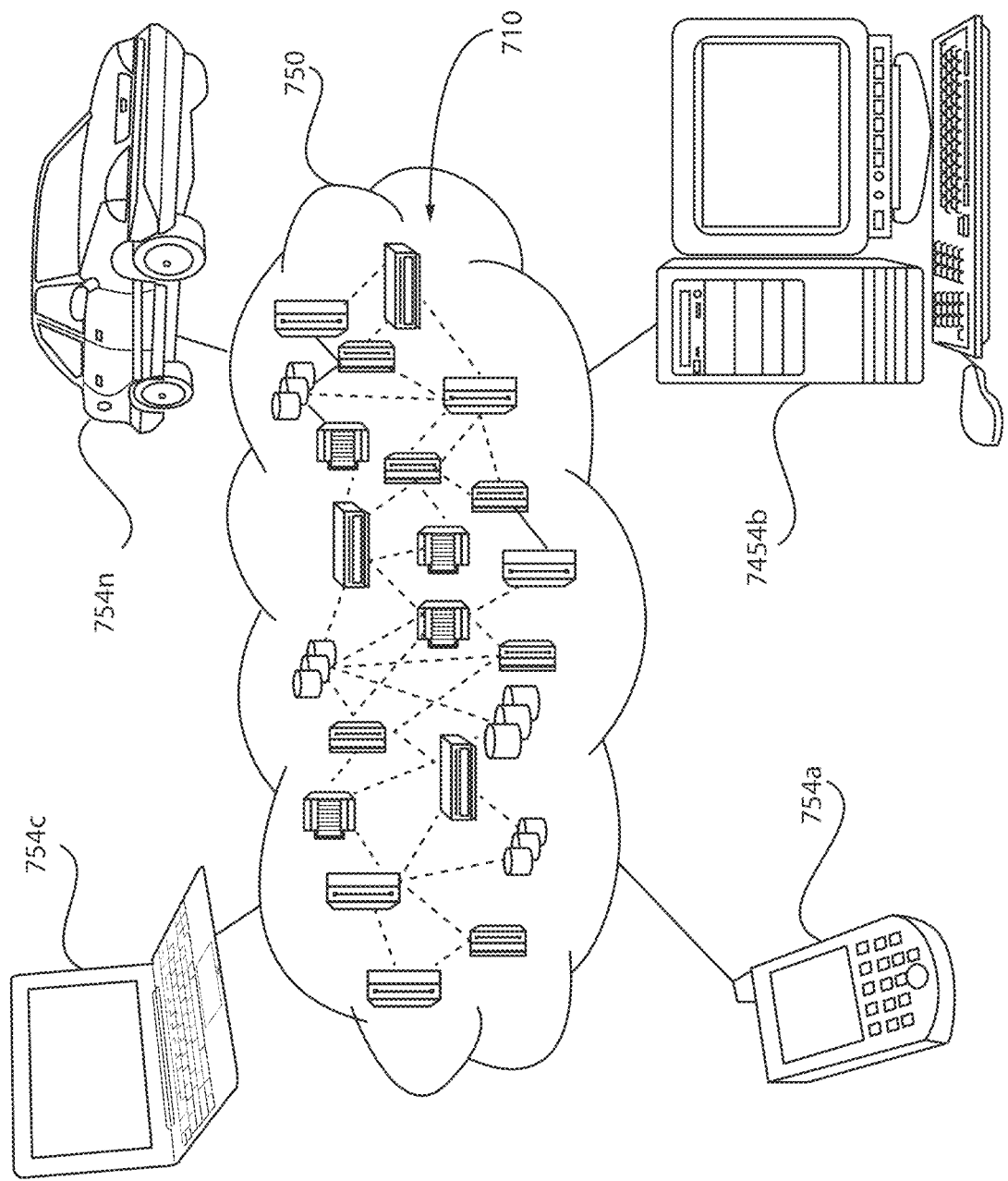
FIG. 7 is a block/flow diagram of an exemplary cloud computing environment, in accordance with an embodiment of the present invention.

FIG. 7 is a block/flow diagram of an exemplary cloud computing environment, in accordance with an embodiment of the present invention.

It is to be understood that although this invention includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 7, illustrative cloud computing environment 750 is depicted for enabling use cases of the present invention. As shown, cloud computing environment 750 includes one or more cloud computing nodes 710 with which local computing devices used by cloud consumers, such as, for example, personal digital assistant (PDA) or cellular telephone 754A, desktop computer 754B, laptop computer 754C, and/or automobile computer system 754N can communicate. Nodes 710 can communicate with one another. They can be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
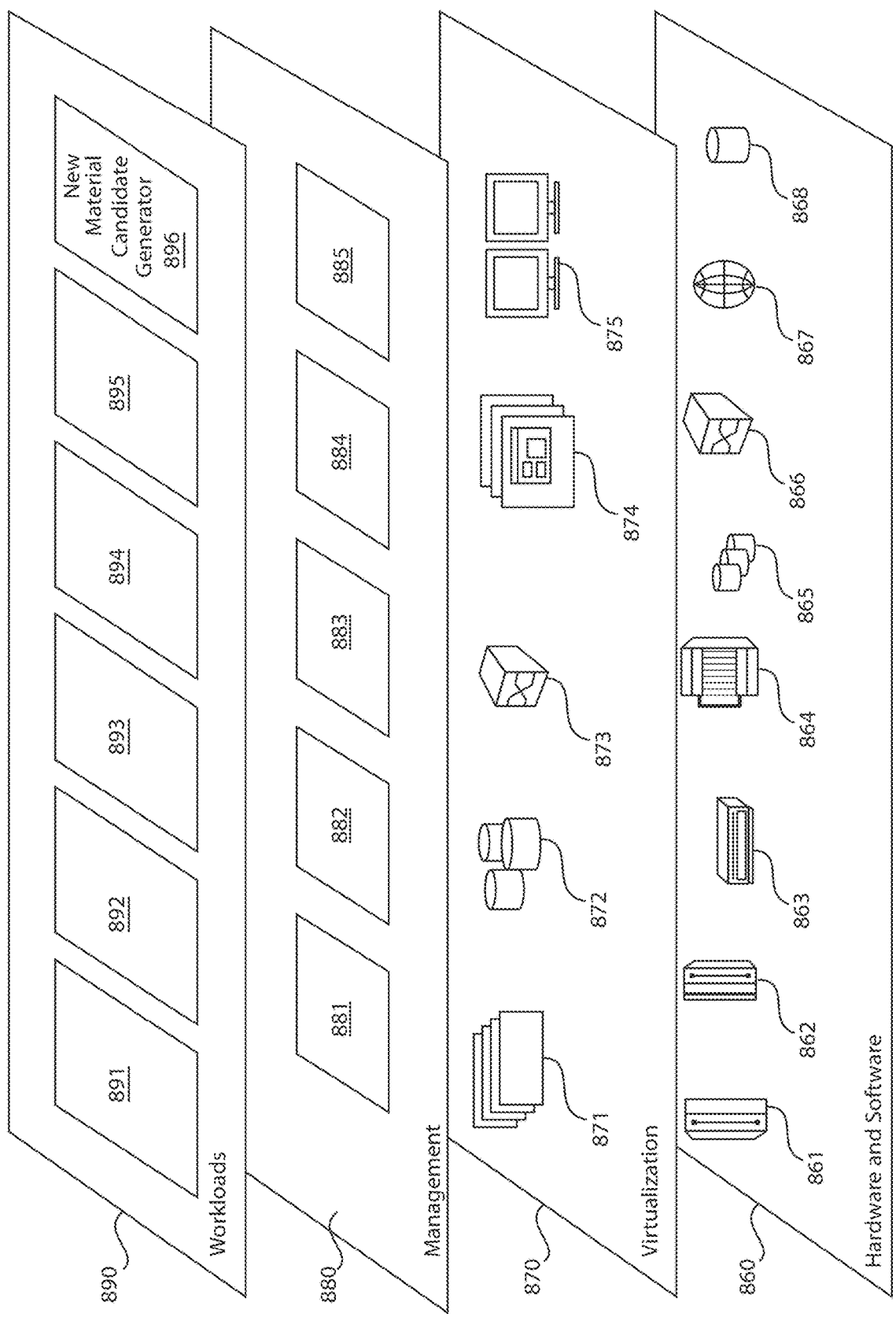
FIG. 8 is a schematic diagram of exemplary abstraction model layers, in accordance with an embodiment of the present invention.

FIG. 8 is a schematic diagram of exemplary abstraction model layers, in accordance with an embodiment of the present invention. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities can be provided: virtual servers 871; virtual storage 872; virtual networks 873, including virtual private networks; virtual applications and operating systems 874; and virtual clients 875.

In one example, management layer 880 can provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment can be utilized. Examples of workloads and functions which can be provided from this layer include: mapping and navigation 891; software development and lifecycle management 892; virtual classroom education delivery 893; data analytics processing 894; transaction processing 895; and a new material candidate generator 896.

As used herein, the terms "data," "content," "information" and similar terms can be used interchangeably to refer to data capable of being captured, transmitted, received, displayed and/or stored in accordance with various example embodiments. Thus, use of any such terms should not be taken to limit the spirit and scope of the disclosure. Further, where a computing device is described herein to receive data from another computing device, the data can be received directly from the another computing device or can be received indirectly via one or more intermediary computing devices, such as, for example, one or more servers, relays, routers, network access points, base stations, and/or the like.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The present invention can be a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to at least one processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks or modules. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks or modules.

The computer readable program instructions can also be loaded onto a computer, other programmable data processing apparatus, or other device to cause a series of operational blocks/steps to be performed on the computer, other programmable apparatus or other device to produce a computer implemented process, such that the instructions which execute on the computer, other programmable apparatus, or other device implement the functions/acts specified in the flowchart and/or block diagram block or blocks or modules.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

Having described preferred embodiments of a system and method for discovering new material candidates from a chemical database (which are intended to be illustrative and not limiting), it is noted that modifications and variations can be made by persons skilled in the art in light of the above teachings. It is therefore to be understood that changes may be made in the particular embodiments described which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method executed on a processor for discovering new material candidates from a chemical database, the method comprising:
    performing deep learning using training data derived from material samples and material simulations that includes:
        extracting a feature vector from a chemical formula;
        training a prediction model using the feature vector with a sparse kernel model employing the training data derived from material samples and material simulations;
        predicting property values from the feature vector using the trained prediction model;
    selecting an existing material from a list of existing materials sorted in descending order based on the predicted property values by the trained prediction model;
    selecting a basis material from a list of basis materials sorted in descending order of absolute reaction magnitudes to the selected existing material;
    generating the new material candidates as variants of the selected existing material with consideration of the selected basis material; and
    outputting the new material candidates on a user interface of a computing device to allow a person to analyze and evaluate the new material candidates to match the new material candidates quickly and efficiently with chemical tasks assigned to the person with less experimental efforts and lower computational costs.

2. The method of claim 1, wherein the generating step further includes:
    in response to a positive reaction, swapping a substructure between the selected existing material and the selected basis material.

3. The method of claim 1, wherein the generating step further includes:
    in response to a negative reaction, subtracting substructures shared between the selected existing material and the selected basis material from the selected existing material.

4. The method of claim 1, wherein the basis material is stored in a training database used to train the prediction model.

5. The method of claim 1, wherein the reaction magnitude is a distance between the selected existing material and the basis material×coefficient of the trained prediction model.

6. The method of claim 1, wherein the new material candidates are discovered in an interpolation area of the trained prediction model.

7. The method of claim 1, wherein the chemical tasks include at least high glass transition temperature tasks, low viscosity tasks, and chemical reaction tasks.

8. A non-transitory computer-readable storage medium comprising a computer-readable program executed on a processor in a data processing system for discovering new material candidates from a chemical database, wherein the computer-readable program when executed on the processor causes a computer to perform the steps of:

performing deep learning, using training, data derived from material samples and material simulations that includes:
        extracting a feature vector from a chemical formula;
        training a prediction model using the feature vector with a sparse kernel model employing the training data derived from material samples and material simulations;
        predicting property values from the feature vector using the trained prediction model;
        selecting an existing material from a list of existing materials sorted in descending order based on the predicted property values by the trained prediction model;
        selecting a basis material from a list of basis materials sorted in descending order of absolute reaction magnitudes to the selected existing material;
        generating the new material candidates as variants of the selected existing material with consideration of the selected basis material; and
        outputting the new material candidates on a user interface of a computing device to allow a person to analyze and evaluate the new material candidates to match the new material candidates quickly and efficiently with chemical tasks assigned to the person with less experimental efforts and lower computational costs.

9. The non-transitory computer-readable storage medium of claim 8, wherein the generating step further includes:
    in response to a positive reaction, swapping a substructure between the selected existing material and the selected basis material.

10. The non-transitory computer-readable storage medium of claim 8, wherein the generating step further includes:
    in response to a negative reaction, subtracting substructures shared between the selected existing material and the selected basis material from the selected existing material.

11. The non-transitory computer-readable storage medium of claim 8, wherein the basis material is stored in a training database used to train the prediction model.

12. The non-transitory computer-readable storage medium of claim 8, wherein the reaction magnitude is a distance between the selected existing material and the basis material×coefficient of the trained prediction model.

13. The non-transitory computer-readable storage medium of claim 8, wherein the new material candidates are discovered in an interpolation area of the trained prediction model.

14. The non-transitory computer-readable storage medium of claim 8, wherein the chemical tasks include at least high glass transition temperature tasks, low viscosity tasks, and chemical reaction tasks.

15. A system for discovering new material candidates from a chemical database, the system comprising:
    a memory; and
    one or more processors in communication with the memory configured to:
        perform deep learning using training data derived from material samples and material simulations that includes:
            extract a feature vector from a chemical formula;
            train a prediction model the feature vector with a sparse kernel model employing the training data derived from material samples and material simulations;
            predict property values from the feature vector using the trained prediction model:
        select an existing material from a list of existing materials sorted in descending order based on the predicted property values by the trained prediction model;
        select a basis material from a list of basis materials sorted in descending order of absolute reaction magnitudes to the selected existing material;
        generate the new material candidates as variants of the selected existing material with consideration of the selected basis material; and
        output the new material candidates on a user interface of a computing device to allow a person to analyze and evaluate the new material candidates to match the new material candidates quickly and efficiently with chemical tasks assigned to the person with less experimental efforts and lower computational costs.

16. The system of claim 15, wherein the generation of the new material candidates includes;
    in response to a positive reaction, swapping a substructure between the selected existing material and the selected basis material.

17. The system of claim 15, wherein the generation of the new material candidates includes:
    in response to a negative reaction, subtracting substructures shared between the selected existing material and the selected basis material from the selected existing material.

18. The system of claim 15, wherein the basis material is stored in a training database used to train the prediction model.

19. The system of claim 15, wherein the reaction magnitude is a distance between the selected existing, material and the basis material×coefficient of the trained prediction model.

20. The system of claim 15, wherein the chemical tasks include at least high glass transition temperature tasks, low viscosity tasks, and chemical reaction tasks.

\* \* \* \* \*